(12) United States Patent
    Chambers et al.

(10) Patent No.: US 12,653,585 B2
(45) Date of Patent: Jun. 16, 2026

---

(54) ADJUSTABLE ANGLE BONE FIXATION ASSEMBLY

(71) Applicant: In2Bones USA, LLC, Memphis, TN (US)

(72) Inventors: Casey M. Chambers, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 92 days.

(21) Appl. No.: 18/370,055

(22) Filed: Sep. 19, 2023

(65) Prior Publication Data

US 2024/0024002 A1     Jan. 25, 2024

Related U.S. Application Data

(63) Continuation of application No. 15/901,781, filed on Feb. 21, 2018, now Pat. No. 11,766,282.

(60) Provisional application No. 62/462,264, filed on Feb. 22, 2017.

(51) Int. Cl.
    *A61B 17/80* (2006.01)
    *A61B 17/86* (2006.01)

(52) U.S. Cl.
    CPC ...... *A61B 17/8057* (2013.01); *A61B 17/8605* (2013.01); *A61B 17/861* (2013.01); *A61B 17/863* (2013.01)

(58) Field of Classification Search
    CPC ..... A61B 17/80; A61B 17/8057; A61B 17/86; A61B 17/861; A61B 17/862; A61B 17/863; A61B 17/8605
    See application file for complete search history.

(56) References Cited

U.S. PATENT DOCUMENTS

| | | | |
|---|---|---|---|
| 8,652,183 B1 * | 2/2014 | Truman | A61B 17/8615 |
| | | | 606/305 |
| 9,265,542 B2 * | 2/2016 | Koay | A61B 17/84 |
| 9,924,984 B2 * | 3/2018 | Hartdegen | A61B 17/8863 |
| 2014/0005728 A1 | 1/2014 | Koay et al. | |
| 2014/0277180 A1 | 9/2014 | Paolino et al. | |
| 2015/0051651 A1 * | 2/2015 | Terrill | A61B 17/8052 |
| | | | 606/289 |
| 2016/0317199 A1 | 11/2016 | Hartdegen et al. | |

* cited by examiner

*Primary Examiner* — Christopher J Beccia
(74) *Attorney, Agent, or Firm* — Rutan & Tucker LLP; Hani Z. Sayed

(57) ABSTRACT

A bone fixation screw is provided for coupling with a bone fusion plate to join bone fusions. The bone fixation screw comprises a head portion and a shank that is comprised of distal threads and extends to a tapered portion and a rounded distal end. The head portion includes proximal threads extending circumferentially around an inferior end of the head portion. The proximal threads are configured to advantageously cross-thread with aperture threads of the bone fusion plate when the bone fixation screw is obliquely angled relative to the bone fusion plate. Slots disposed around the head portion allow the proximal threads to disengage and reengage with the aperture threads as the bone fixation screw turns. A shaped opening in a superior end of the head portion engagedly receives a tool for driving the bone fixation screw into a bone hole.

20 Claims, 4 Drawing Sheets

ADJUSTABLE ANGLE BONE FIXATION ASSEMBLY

PRIORITY

This application claims the benefit of and priority to U.S. patent application Ser. No. 15/901,781, filed on Feb. 21, 2018 and U.S. Provisional Application, entitled "Adjustable Angle Bone Fixation Assembly," filed on Feb. 22, 2017 and having application Ser. No. 62/462,264.

FIELD

The field of the present disclosure generally relates to securing bones together. More particularly, the field of the present disclosure relates to an apparatus for fusing and compressing bones of the human body.

BACKGROUND

A fusion bone plate implant may be utilized in conjunction with one or more fasteners so as to generate compression and stability at a bone interface. An implant coupled with fasteners generally serves to stabilize bones, or bone parts, relative to one another so as to promote bone fusion. In many applications, bone plates and fasteners are used to fuse bones, or bone parts, of the human body, such as bones in the foot, the ankle, the hand, the wrist, as well as various other portions of the body. Furthermore, during the course of certain medical procedures, a surgeon may immobilize one or more bones or the bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus is provided for a bone fixation screw to couple with a bone fusion plate for joining bone fusions. The bone fixation screw is comprised of a head portion and a shank that includes distal threads and extends to a tapered portion and a rounded distal end. The head portion includes proximal threads extending circumferentially around an inferior end of the head portion. The proximal threads are configured to advantageously cross-thread with aperture threads of the bone fusion plate when the bone fixation screw is obliquely angled relative to the bone fusion plate. Slots are disposed around the head portion to allow the proximal threads to disengage and reengage with the aperture threads as the bone fixation screw turns. A shaped opening in a superior end of the head portion engagedly receives a tool for driving the bone fixation screw into a bone hole.

In an exemplary embodiment, a bone fixation screw configured to couple with a bone fusion plate for joining bone fusions comprises: a head portion comprised of a superior end and an inferior end comprising proximal threads extending circumferentially around the head portion; a shank extending from the inferior end and comprising distal threads; a tapered portion of the shank extending to a rounded distal end; and a shaped opening disposed in the superior end and configured to engagedly receive a tool suitable for driving the bone fixation screw into a bone hole.

In another exemplary embodiment, the proximal threads are configured to threadably couple with one or more aperture threads disposed circumferentially around an interior of a fixation aperture of the bone fusion plate. In an exemplary embodiment, the one or more aperture threads and the proximal threads share a substantially similar thread pitch. In an exemplary embodiment, the bone fixation screw is configured to be coupled with the fixation aperture at an oblique angle with respect to the bone fusion plate. In an exemplary embodiment, the superior end is disposed at the oblique angle with respect to the plane of the bone fusion plate, such that a countersunk side of the head portion threads deeper into the fixation aperture than a protruding side of the head portion. In an exemplary embodiment, adjacent proximal threads that share a portion of a single aperture thread at the countersunk side share a portion of a different aperture thread at the protruding side. In an exemplary embodiment, the aperture threads and the proximal threads advantageously cross-thread when the bone fixation screw is obliquely angled relative to the bone fusion plate.

In an exemplary embodiment, the bone fixation screw further comprises a multiplicity of slots that are uniformly disposed around the perimeter of the head portion. In an exemplary embodiment, the multiplicity of slots are configured to allow the proximal threads and one or more aperture threads disposed circumferentially around an interior of a fixation aperture of the bone fusion plate to disengage and reengage with one another as the bone fixation screw is turned in the fixation aperture. In an exemplary embodiment, the multiplicity of slots is comprised of six cylindrically-shaped cutout portions that are disposed uniformly around the perimeter of the head portion, forming an inverse cloverleaf shape of the superior end. In an exemplary embodiment, each of the multiplicity of slots is comprised of an angled cutout portion that is disposed on the perimeter of the head portion. In an exemplary embodiment, each of the multiplicity of slots is comprised of square-shaped cutouts that is disposed on the perimeter of the head portion. In an exemplary embodiment, one or more portions comprising the multiplicity of slots may be comprised of different shaped cutouts that are arranged around the perimeter of the head portion. In an exemplary embodiment, each of a first portion of the multiplicity of slots is comprised of a first shape and each of a second portion of the multiplicity of slots is comprised of a second shape, and wherein the first portion and the second portion are disposed in an alternating arrangement around the head portion. In an exemplary embodiment, a number of slots comprising the multiplicity of slots depends on a shape and a size of the shaped opening.

In an exemplary embodiment, the shaped opening has a size and a shape that cooperates with an arrangement of a multiplicity of slots that are uniformly disposed around the perimeter of the head portion. In an exemplary embodiment, peripheral regions comprising the shaped opening and having the greatest diameter of the shaped opening are axially oriented between adjacent of the multiplicity of slots, such that the peripheral regions are disposed in relatively thicker regions of the head portion, such that the overall size of the shaped opening may be maximized without compromising the structural integrity of the head portion. In an exemplary embodiment, the shaped opening is comprised of a hexalobe shape that is substantially concentric with the head portion and the shank.

In an exemplary embodiment, the proximal threads are comprised of a thread pitch that is substantially the same as the thread pitch comprising one or more aperture threads that are disposed circumferentially around an interior of a fixation aperture of the bone fusion plate. In an exemplary embodiment, the proximal threads are configured to have substantially one-half of a mating thread size of one or more aperture threads. In an exemplary embodiment, the thread pitch is selected to facilitate engaging the bone fixation screw within the fixation aperture at an oblique angle with respect to the bone fusion plate.

In an exemplary embodiment, the distal threads angulate along the shank and terminate in the tapered portion. In an exemplary embodiment, the distal threads are configured to rotatably engage within a suitably sized hole drilled in a patient's bone. In an exemplary embodiment, turning the bone fixation screw in an appropriate direction by way of a tool coupled with the shaped opening, drives the distal threads to engage with bone tissue surrounding the bone hole, thereby advancing the bone fixation screw deeper into the bone hole. In an exemplary embodiment, the tapered portion and the rounded distal end are configured to guide the bone fixation screw through the bone hole with relatively little resistance.

In an exemplary embodiment, one or more flutes extend along the shank from adjacent of the rounded distal end and into the distal threads. In an exemplary embodiment, at least one cutting edge borders each of the one or more flutes, the at least one cutting edge being configured to advantageously clean the interior of the bone hole and increase the diameter of the hole to accept the distal threads of the advancing bone fixation screw. In an exemplary embodiment, the one or more flutes spiral along a portion of the shank, the spiral being configured so as to control a rate of bone debris removal from the interior of the bone hole during rotation of the bone fixation screw.

BRIEF DESCRIPTION OF THE DRAWINGS

The drawings refer to embodiments of the present disclosure in which.

Figures 1, 2:
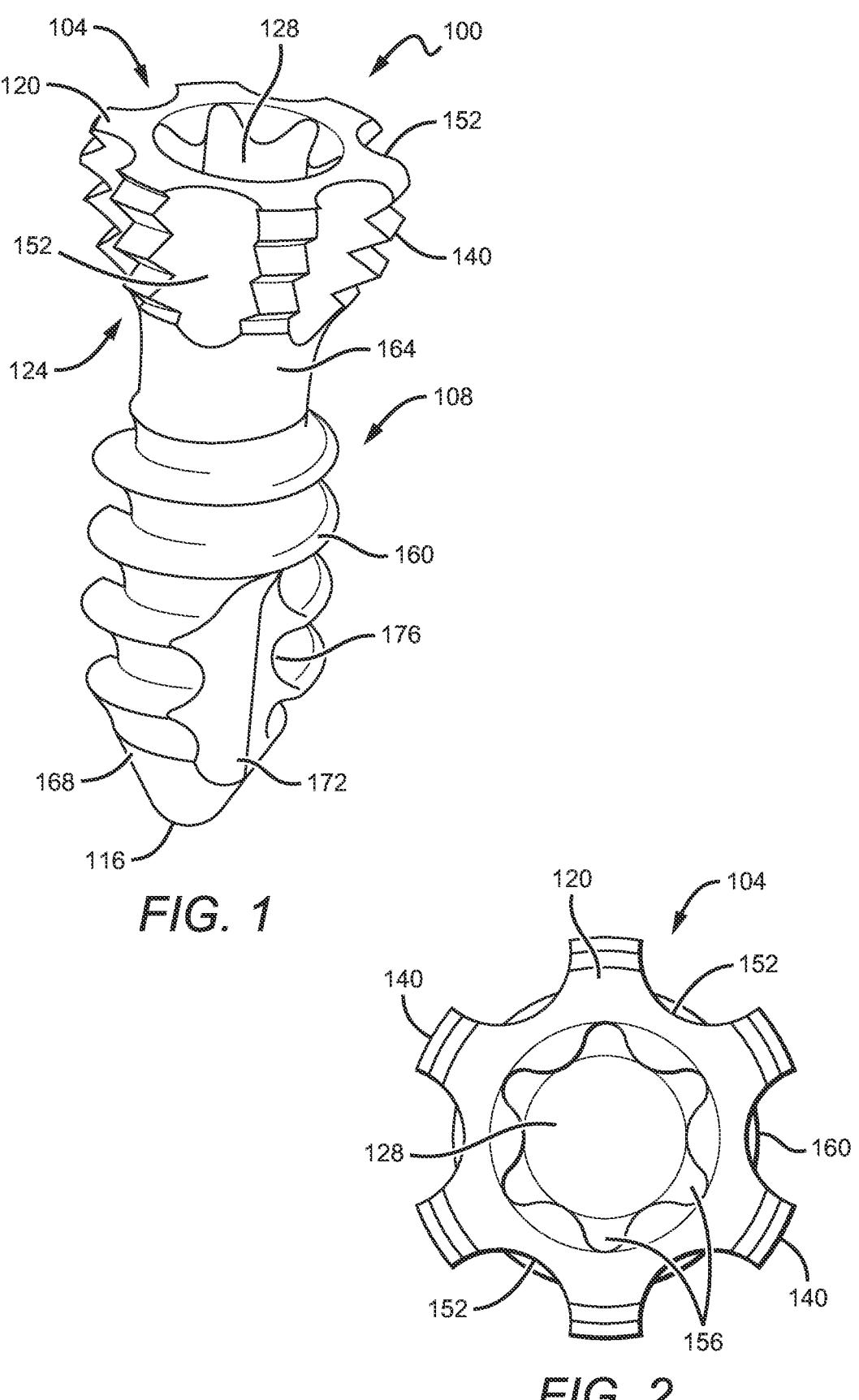
FIG. 1 illustrates an isometric view of an exemplary embodiment of a bone fixation screw that may be used for repairing bone fractures, fixating osteotomies, and joining fusions of the skeletal system.
FIG. 2 illustrates a top plan view of the bone fixation screw of FIG. 1, showing a head portion and a shaped opening of the bone fixation screw.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first screw," may be made. However, the specific numeric reference should not be interpreted as a literal sequential order but rather interpreted that the "first screw" is different than a "second screw." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus for a bone fixation screw that is configured to couple with a bone fusion plate for joining bone fusions. The bone fixation screw comprises a head portion and shank. The head portion is comprised of a superior end and an inferior end that includes proximal threads extending circumferentially around the head portion. The proximal threads are configured to advantageously cross-thread with aperture threads of the bone fusion plate when the bone fixation screw is obliquely angled relative to the bone fusion plate. A multiplicity of slots disposed around the perimeter of the head portion are configured to allow the proximal threads to disengage and reengage with the aperture threads as the bone fixation screw is turned. The shank extends from the inferior end and is comprised of distal threads. A tapered portion of the shank extending to a rounded distal end are configured to guide the bone fixation screw with relatively little resistance through a bone hole drilled in a patient's bone. In some embodiments, flutes and cutting edges may be disposed near the distal end to facilitate clearing bone debris from the hole as the bone fixation screw turns. A shaped opening is disposed in the superior end and configured to engagedly receive a tool suitable for driving the bone fixation screw into the bone hole.

FIGS. 1-2 illustrate an exemplary embodiment of a bone fixation screw 100 that may be used for repairing bone fractures, fixating osteotomies, joining fusions of the skeletal system, and the like. It should be understood that the terms "bone fixation screw," "bone screw," "fastener," "fixator," "elongate member," and "screw" may be used interchangeably herein as they essentially describe the same type of device. The bone fixation screw 100 generally is an elongate member comprised of a head portion 104 and a shank 108 having a rounded distal end 116. The head portion 104 is comprised of a superior end 120 and an inferior end 124. As best illustrated in FIG. 2, the superior end 120 includes a shaped opening 128 that is substantially concentric with the head portion 104 and the shank 108. The shaped opening 128 generally is configured to engagedly receive a tool suitable for driving the bone fixation screw 100 into a hole drilled in a patient's bone. Although the shaped opening 128 in the illustrated embodiment is comprised of a hexalobe shape, any of various multi-lobe shapes, as well as other polygonal shapes, are also contemplated.

Figure 3:
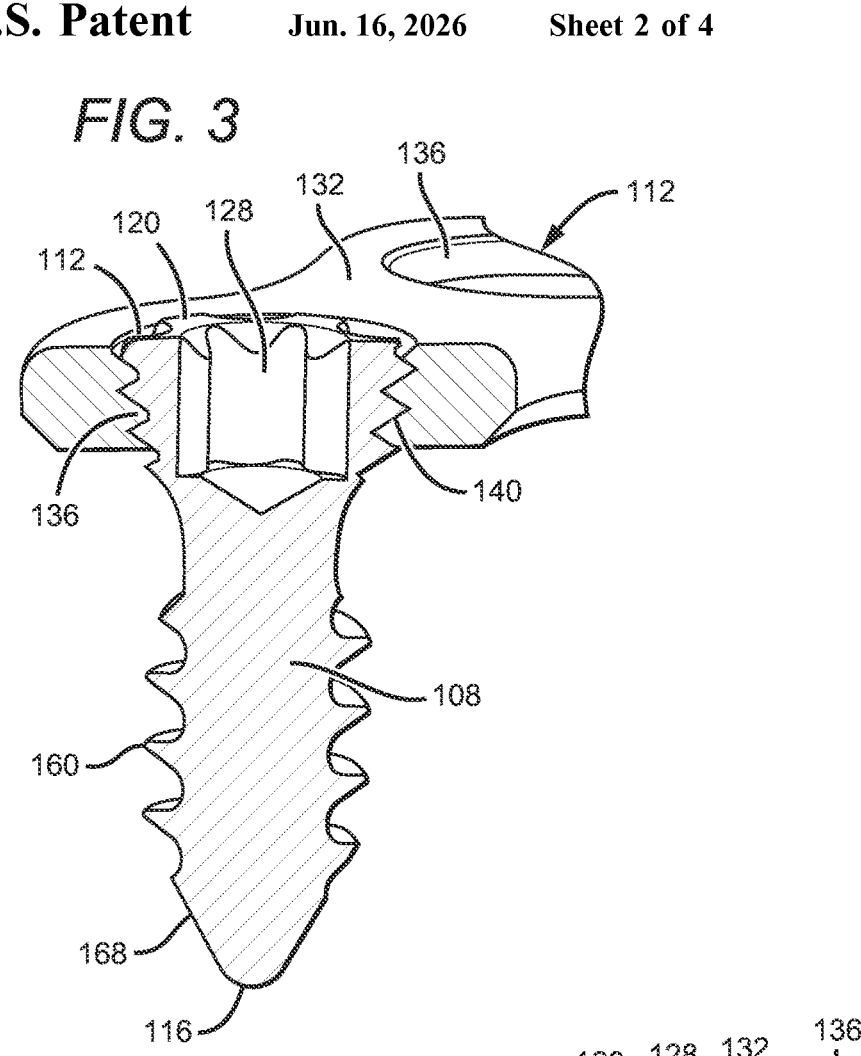
FIG. 3 illustrates a cross-sectional view of the bone fixation screw of FIG. 1 disposed within a fixation aperture of a bone fusion plate at a substantially right angle with respect to the bone fusion plate.

As best illustrated in FIG. 3, the inferior end 124 is generally configured to threadably countersink within a fixation aperture 112 of a bone fusion plate 132. The bone fusion plate 132 is configured to be coupled with adjacent bones, across a bone fusion site, so as to fixate the bones and encourage fusion of the bones. The bone fusion plate 132 may be advantageously used for repairing bone fractures, fixating osteotomies, joining fusions of the skeletal system, and the like. The bone fusion plate 132 comprises a generally elongate member having multiple fixation apertures 112 that are configured to receive fixation bone screws 100, such that the bone screws may be coupled with the adjacent bones on opposite sides of a bone fusion site, such as, for example, a bone fracture to be fused. The bone fusion plate 132 may be implemented with one or more directions, or degrees, of curvature such that the plate matches an anatomical shape of a target bone to which the bone fusion plate is to be coupled. For example, the bone fusion plate 132 may be curved in a longitudinal direction and/or a lateral direction, without limitation. The bone fusion plate 132 may be comprised of a semi-rigid material, such as a biocompatible metal or PEEK, possessing a tensile strength suitable for immobilizing adjacent bone parts of the human body.

The fixation apertures 112 each comprises one or more aperture threads 136 that extend circumferentially around an interior of the fixation aperture. The aperture threads 136 are configured to threadably engage with proximal threads 140 disposed on the inferior end 124 circumferentially around the head portion 104 of the bone fixation screw 100. As such, in the illustrated embodiment of FIG. 3, the aperture threads 136 and the proximal threads 140 share a substantially similar thread pitch. Thus, turning the bone fixation screw 100 in an appropriate direction countersinks the head portion 104 into the fixation aperture 112, as shown in FIG. 3, as well as securing the bone fixation screw to the bone fusion plate 132. As will be appreciated, limiting protrusion of the head portion 104 above the bone fusion plate 132 may advantageously minimize irritation to nearby soft tissue that may otherwise occur due to a relatively greater presence of the head portion.

Figure 4:
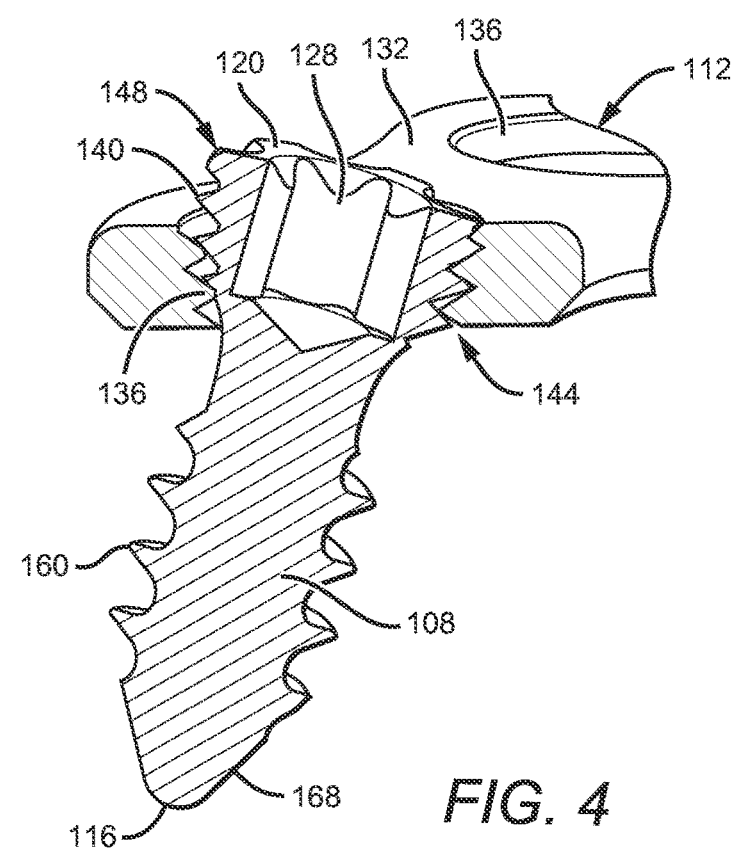
FIG. 4 illustrates a cross-sectional view of the bone fixation screw of FIG. 1 disposed within the fixation aperture of the bone fusion plate at an oblique angle with respect to the bone fusion plate.

Although the fixation aperture 112 may receive the bone fixation screw 100 at a substantially right angle with respect to the bone fusion plate 132, as shown in FIG. 3, the bone fixation screw may also be coupled with the fixation aperture at an oblique angle as shown in FIG. 4. As will be recognized, when the bone fixation screw 100 is coupled at a right angle relative to the bone fusion plate 132, each of the aperture threads 136 is received between adjacent proximal threads 140, and the superior end 120 is substantially co-planar with the bone fusion plate 132, as shown in FIG. 3. In an oblique configuration, however, the superior end 120 is disposed at an oblique angle with respect to the plane of the bone fusion plate 132. Thus, a countersunk side 144 of the head portion 104 threads deeper into the fixation aperture 112 than a protruding side 148 of the head portion 104, as shown in FIG. 4. Consequently, adjacent proximal threads 140 that share a portion of a single aperture thread 136 at the countersunk side 144 share a portion of a different aperture thread 136 at the protruding side 148. Thus, the aperture threads 136 and the proximal threads 140 advantageously cross-thread when the bone fixation screw 100 is obliquely angled relative to the bone fusion plate 132.

As shown in FIGS. 1-2, a multiplicity of slots 152, or cutouts, are uniformly disposed around the perimeter of the head portion 104. The slots 152 serve to allow the aperture threads 136 and the proximal threads 140 to disengage and reengage with one another as the bone fixation screw 100 is turned in the fixation aperture 112. Disengaging and then reengaging the threads 136, 140, by way of the slots 152, allows the threads to cross-thread without being damaged. In one embodiment, for example, during turning the bone fixation screw 100, the slots 152 allow adjacent proximal threads 140 to disengage from a first aperture thread 136, that was engaged along the countersunk side 144, and engage a second aperture thread along the protruding side 148. As the bone fixation screw 100 continues turning, the slots 152 allow the adjacent proximal threads 140 to disengage from the second aperture thread 136 and reengage the first aperture thread along the countersunk side 144.

In the illustrated embodiment of FIG. 2, six of the slots 152 are disposed uniformly around the perimeter of the head portion 104, and each of the slots 152 comprises a cylindrically-shaped cutout portion, giving the superior end 120 an inverse cloverleaf shape. Other shapes of the slots 152 are contemplated, however. For example, in one embodiment, each of the slots 152 may comprise an angled cutout portion. In one embodiment, each of the slots 152 may be comprised of square-shaped cutouts. Still, in some embodiments, one or more portions of the slots 152 may be comprised of different shaped cutouts. In one embodiment, for example, half of the slots 152 disposed on the head portion 104 may be cylindrical and half of the slots may be angular cutouts. Further, differently-shaped slots 152 may be disposed on the head portion 104 in various arrangements, without limitation. In one embodiment, for example, the slots 152 may be cylindrical and angular cutouts in an alternating arrangement around the head portion 104. Moreover, it should be understood that either more than or less than six of the slots 152 may be incorporated into the head portion 104 without limitation. Further, in some embodiments, the number of slots 152 disposed in the head portion 104 may depend on the particular shape that is selected for the shaped opening 128, as well as the overall size of the selected shape comprising the shaped opening.

As will be appreciated, the above-mentioned first aperture thread 136 generally is disposed relatively deeper in the fixation aperture 112 than the second aperture thread 136. In one embodiment, the first and second aperture threads 136 are adjacent to one another. In some embodiments, however, one or more aperture threads 136 may be disposed between the first and second aperture threads. It should be understood that the number of aperture threads 136 that may be disposed between the first and second aperture threads generally will depend upon the angle between the bone fixation screw 100 and the bone fusion plate 132, as well as the specific characteristics of the aperture and proximal threads 136, 140, such as, for example, the thread pitch, and thus the number of aperture threads 136 that may be disposed between the first and second aperture threads may be varied without limitation.

Upon referring to FIG. 2, it will be observed that the shaped opening 128 coincides with the disposition of the slots 152 around the perimeter of the head portion 104. In particular, peripheral regions 156 of the shaped opening 128 having the greatest diameter are axially oriented between the slots 152, and thus the peripheral regions 156 are disposed in relatively thicker regions of the head portion 104. It is contemplated that, is some embodiments, axially aligning the peripheral regions 156 with the regions comprising the proximal threads 140 advantageously facilitates maximizing the overall size of the shaped opening 128 without compromising the structure integrity of the head portion 104. It is further contemplated that the peripheral regions 156 comprising shapes other than the shaped opening 128 illustrated herein may be axially aligned, and the size of the shape may be maximized, as described herein, without limitation.

Referring again to FIG. 1, the shank 108 is comprised of distal threads 160 that share a smooth portion 164 with the proximal threads 140. The distal threads 160 angulate along the shank 108 and terminate in a tapered portion 168 that extends to the rounded distal end 116. The tapered portion 168 and the rounded distal end 116 are configured to facilitate guiding the bone fixation screw 100 through a bone hole with relatively little resistance. The distal threads 160 are configured to rotatably engage within a suitably sized hole drilled in the patient's bone. Thus, turning the bone fixation screw 100 in an appropriate direction by way of a tool coupled with the shaped opening 128, drives the distal threads 160 to engage with bone tissue surrounding the hole, advancing the bone fixation screw 100 deeper into the hole in the bone. Further, the proximal threads 140 engage with the aperture threads 136 once a majority of the bone fixation screw 100 is already disposed within the bone hole. Continued turning of the bone fixation screw 100 then countersinks the inferior end 124 into fixation aperture 112, as described herein.

The rounded distal end 116 and the tapered portion 168 of the bone fixation screw 100 are further comprised of one or more flutes 172 that extend along the shank 108 from adjacent of the rounded distal end 116 and into the distal threads 160. At least one cutting edge 176 borders each of the flutes 172. Although the illustrated embodiment of the bone fixation screw 100 comprises two flutes 172, and thus two cutting edges 176, more than or less than two flutes 172 and two cutting edges 176 may be incorporated into different implementations of the bone fixation screw 100 without limitation. As will be appreciated, the cutting edges 176 advantageously clean the interior of the bone hole and increase the diameter of the hole to accept the distal threads 160 of the advancing bone fixation screw 100. It is contemplated that, in some embodiments, the flutes 172 may spiral, or twist, along a portion of the shank 108 so as to generally control the rate of bone debris removal from the interior of the bone hole during rotation of the bone fixation screw 100. It is further contemplated that the flutes 172 may be implemented with any of various spirals without deviating beyond the spirit and scope of the present disclosure.

Figure 5:
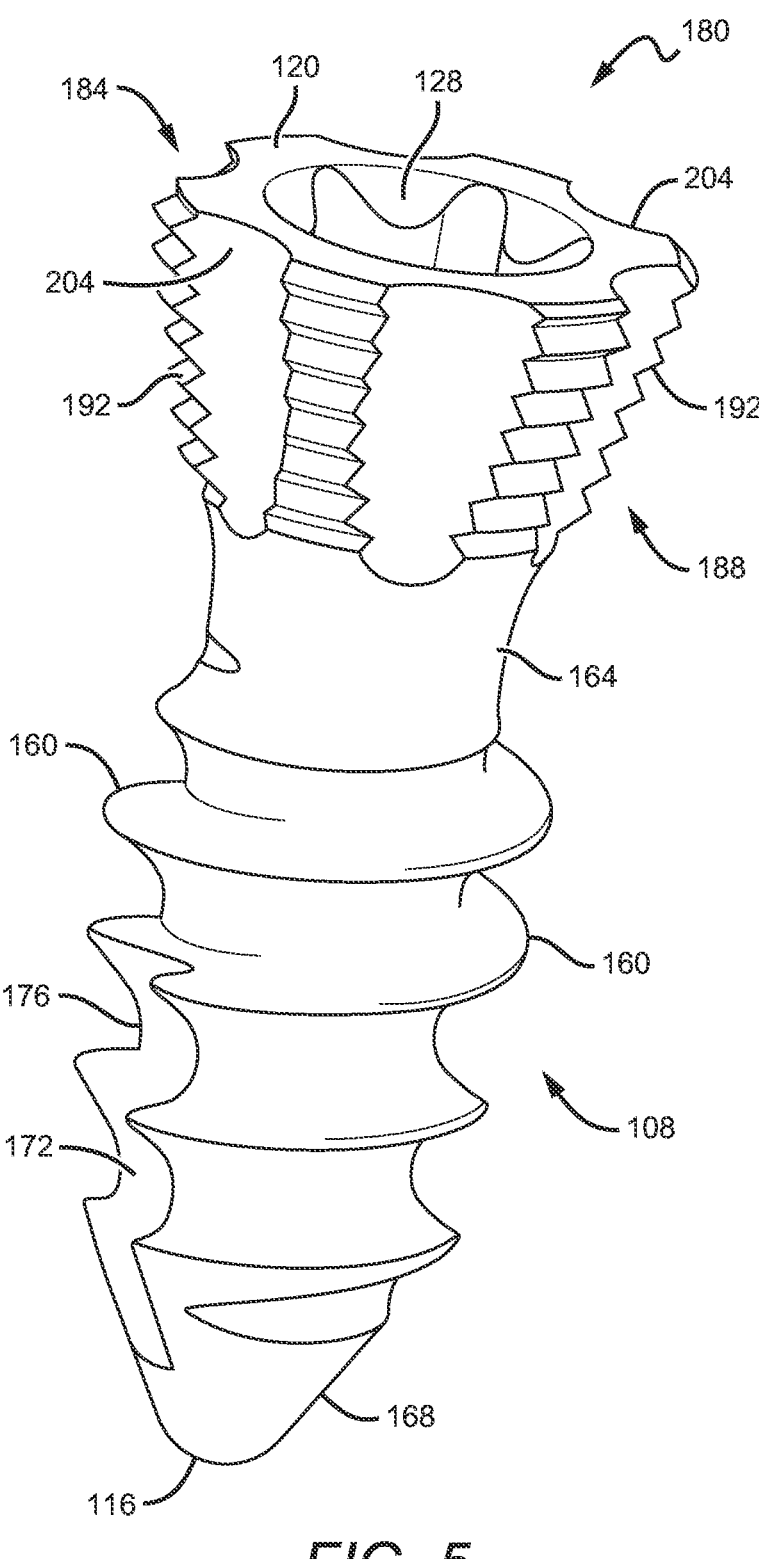
FIG. 5 illustrates an isometric view of an exemplary embodiment of a bone fixation screw that may be used to repair bone fractures, fixating osteotomies, and joining fusions of the skeletal system.

FIG. 5 illustrates an isometric view of an exemplary embodiment of bone fixation screw 180 may be used for repairing bone fractures, fixating osteotomies, joining fusions of the skeletal system, and the like. The bone fixation screw 180 is substantially similar to the bone fixation screw 100, illustrated in FIG. 1, with the exception that a head portion 184 of the bone fixation screw 180 is comprised of an inferior end 188 having proximal threads 192 that are smaller and more numerous than the proximal threads 140. Like the inferior end 124 of FIG. 1, the inferior end 184 is configured to threadably countersink within the fixation aperture 112 of the bone fusion plate 132. In the embodiment illustrated in FIG. 5, however, the proximal threads 192 are configured to have substantially the same thread pitch, and about one-half of the mating thread size of the aperture threads 136.

Figures 6, 7:
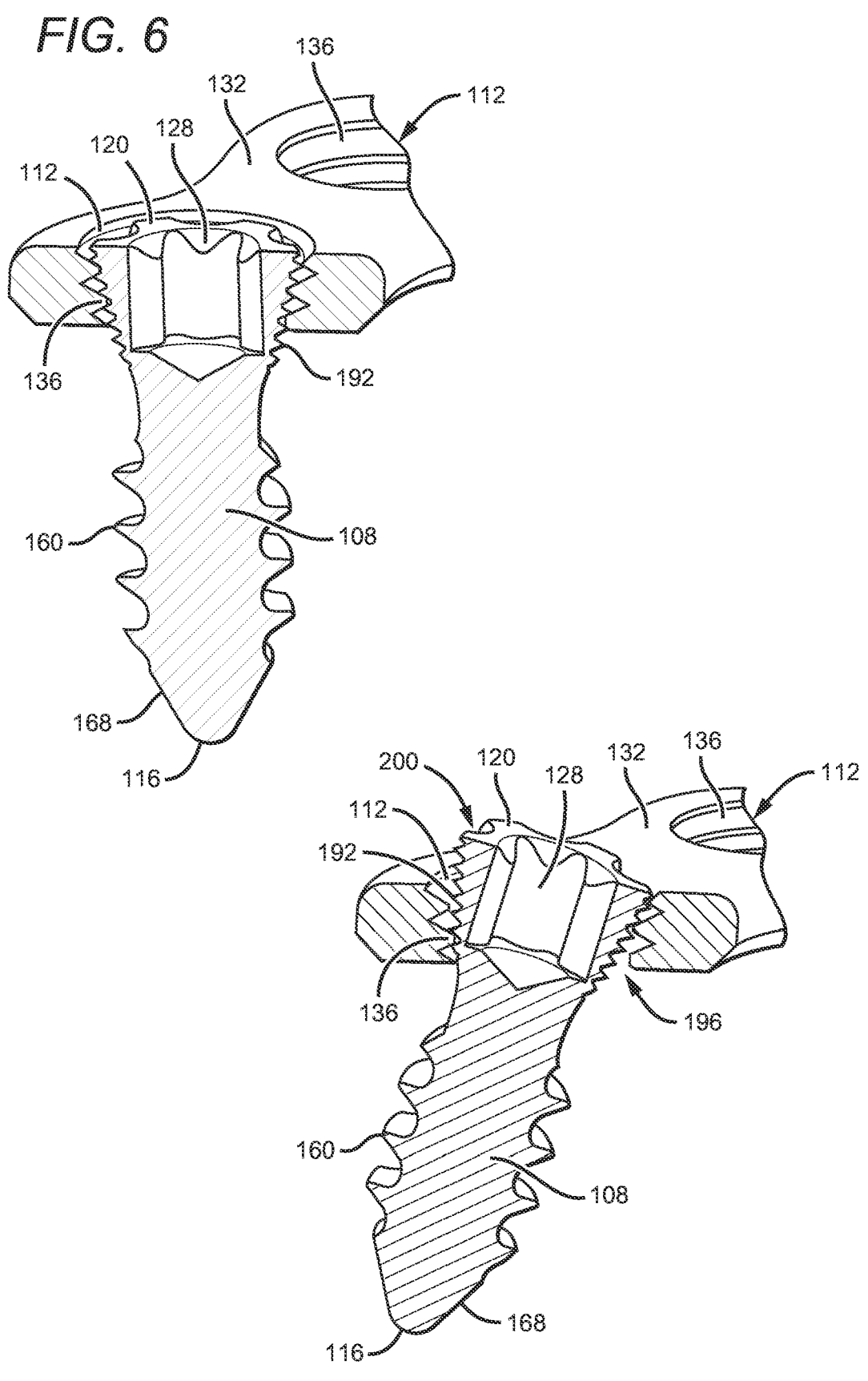
FIG. 6 illustrates a cross-sectional view of the bone fixation screw of FIG. 5 disposed within a fixation aperture of a bone fusion plate at a substantially right angle with respect to the bone fusion plate.
FIG. 7 illustrates a cross-sectional view of the bone fixation screw of FIG. 5 disposed within the fixation aperture of the bone fusion plate at an oblique angle with respect to the bone fusion plate.

As shown in FIGS. 6-7, the shared thread pitch of the proximal threads 192 and the aperture threads 136 facilitates engaging the bone fixation screw 180 with the bone fusion plate 132 despite the relatively smaller mating size of the proximal threads. Thus, the fixation aperture 112 may receive the bone fixation screw 180 at a substantially right angle with respect to the bone fusion plate 132, as shown in FIG. 6, as well as in an oblique configuration as shown in FIG. 7. In the oblique configuration, a countersunk side 196 of the head portion 184 threads deeper into the fixation aperture 112 than a protruding side 200 of the head portion 184, and thus more than one adjacent proximal thread 140 may be disposed between adjacent aperture threads 136. A multiplicity of slots 204 disposed uniformly around the perimeter of the inferior end 188 allow the proximal threads 192 and the aperture threads 136 to advantageously cross-thread, as described herein. As the bone fixation screw 180 is turned within the fixation aperture 112, the proximal threads 192 and the aperture threads 136 disengage and reengage as proximal thread portions at the countersunk side 196 are moved toward the protruding side 200 and then back toward the countersunk side. Thus, the slots 204 allow the proximal threads 192 and the aperture threads 136 to cross-thread without being damaged.

As will be appreciated, the relationship between the locations of the slots 204 and the peripheral regions 156 of the shaped opening 128 is substantially similar to the relationship between the slots 152 and the shaped opening, discussed with respect to FIG. 2. In particular, the peripheral regions 156 may be axially oriented between the slots 204, such that the peripheral regions 156 are disposed in relatively thicker regions of the head portion 184. It is contemplated, therefore, that axially aligning the peripheral regions 156 with thicker regions of the head portion 184 enables the incorporation of a relatively large shaped opening 128 without compromising the structure integrity of the head portion 184. Further, as discussed herein, the peripheral regions 156 may be comprised of shapes other than the shaped opening 128 illustrated herein and may be axially aligned, without limitation, and without deviation beyond the spirit and scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A method for a bone fixation screw to couple with a bone fusion plate, comprising:
   providing a bone fusion plate and configuring a head portion for engaging a fixation aperture of the bone fusion plate wherein the bone fixation screw is configured to be coupled with the fixation aperture at an oblique angle with respect to the bone fusion plate;
   the bone fusion plate having at least an aperture to receive a bone fixation screw wherein the bone fixation screw is configured to be coupled with the fixation aperture at an oblique angle with respect to the bone fusion plate;
   providing the bone fixation screw comprising a head portion comprised of a superior end and an inferior end, the head portion having at least a proximal thread extending circumferentially around the head portion;

extending a shank distally from the head portion and providing a tapered portion of the shank extending to a distal end and having a plurality of flutes thereon providing a tapered portion of the shank extending to a rounded distal end comprising the plurality of flutes that extend along the shank adjacent of the rounded distal end and into the distal threads wherein flute corresponding to and bordering a cutting edge wherein at least one the cutting edge borders each of the one or more flutes and is configured to clean an interior of the bone hole and increase a diameter of the bone hole to accept the distal threads of the bone fixation screw;

disposing distal threads on the shank for engaging with bone wherein a portion of the distal threads extends past a region formed by at least one of a multiplicity of uniformly disposed slots wherein a portion of the distal threads extends past a region formed by at least one of the multiplicity of uniformly disposed slots;

terminating a tapered portion of the shank at a rounded distal end; and disposing a multiplicity of slots around a perimeter of the head portion.

2. The method of claim 1, wherein configuring the head portion includes configuring a shaped opening on a superior end of the head portion for engagedly receiving a tool suitable for driving the bone fixation screw into a bone hole.

3. The method of claim 1, wherein configuring the head portion includes configuring proximal threads on an inferior end of the head portion for threadably coupling with one or more aperture threads disposed within the fixation aperture.

4. The method of claim 3, wherein configuring the proximal threads includes configuring a thread pitch of the proximal threads to be substantially similar to a thread pitch of the one or more aperture threads.

5. The method of claim 3, wherein configuring the proximal threads includes configuring the head portion to couple with the fixation aperture at an oblique angle with respect to the bone fusion plate, such that a countersunk side of the head portion threads deeper into the fixation aperture than a protruding side of the head portion.

6. The method of claim 5, wherein configuring the proximal threads includes configuring adjacent proximal threads to share a portion of a first aperture thread at the countersunk side and share a portion of a second aperture thread at the protruding side.

7. The method of claim 5, wherein configuring the proximal threads includes configuring the proximal threads to cross-thread with the aperture threads when the bone fixation screw is obliquely angled relative to the bone fusion plate.

8. The method of claim 1, wherein disposing the multiplicity of slots includes configuring the multiplicity of slots to allow the proximal threads to disengage and reengage with the fixation aperture when the bone fixation screw is turned while obliquely angled relative to the bone fusion plate.

9. The method of claim 8, wherein disposing the multiplicity of slots includes disposing six cylindrically shaped cutout portions uniformly around the perimeter of the head portion.

10. The method of claim 8, wherein disposing the multiplicity of slots includes disposing a multiplicity of angled cutout portions around the perimeter of the head portion.

11. The method of claim 8, wherein disposing the multiplicity of slots includes disposing a multiplicity of square-shaped cutouts around the perimeter of the head portion.

12. The method of claim 8, wherein disposing the multiplicity of slots includes disposing differently shaped cutouts around the perimeter of the head portion.

13. The method of claim 12, wherein disposing differently shaped cutouts includes disposing a first portion of the multiplicity of slots comprising a first shape and disposing a second portion of the multiplicity of slots comprising a second shape that is different than the first shape.

14. The method of claim 13, wherein disposing the first portion and disposing the second portion comprises disposing the first portion and the second portion in an alternating arrangement around the head portion.

15. The method of claim 1, wherein configuring the head portion includes configuring a shaped opening having a size and a shape that cooperates with an arrangement of the multiplicity of slots.

16. The method of claim 15, wherein configuring the shaped opening includes orienting peripheral regions of the shaped opening between adjacent slots comprising the multiplicity of slots.

17. The method of claim 15, wherein configuring the shaped opening includes configuring a hexalobe shape that is substantially concentric with the head portion and the shank.

18. The method of claim 1, wherein configuring the head portion includes configuring proximal threads having a thread pitch that is substantially the same as a thread pitch of one or more aperture threads disposed within the fixation aperture of the bone fusion plate.

19. The method of claim 18, wherein configuring the proximal threads includes configuring the proximal threads to have substantially one-half of a mating thread size of one or more aperture threads.

20. The method of claim 19, wherein configuring the proximal threads includes selecting the thread pitch to facilitate engaging the bone fixation screw within the fixation aperture at an oblique angle with respect to the bone fusion plate.

\*    \*    \*    \*    \*